United States Patent [19]

Imanishi et al.

[11] 4,198,514

[45] Apr. 15, 1980

[54] LACTAM COMPOUNDS

[75] Inventors: Masayuki Imanishi, Kawanishi; Yutaka Masuoka, Suita; Ryoko Nakajima, Kobe, all of Japan

[73] Assignee: Takeda Chemical Industries, Ltd., Japan

[21] Appl. No.: 950,524

[22] Filed: Oct. 11, 1978

[30] Foreign Application Priority Data

Oct. 11, 1977 [JP] Japan .................................. 52/122249
Jul. 17, 1978 [JP] Japan .................................... 53/87533

[51] Int. Cl.² .................. C07D 207/20; C07D 213/26
[52] U.S. Cl. ............................ 546/216; 260/326.5 FL
[58] Field of Search ............... 546/216; 260/326.5 FL

[56] References Cited

U.S. PATENT DOCUMENTS

| | | | |
|---|---|---|---|
| 3,317,390 | 5/1967 | Hofmann | 260/326.5 FL |
| 3,935,217 | 1/1976 | Nakanishi | 260/326.5 R |

FOREIGN PATENT DOCUMENTS

| | | | |
|---|---|---|---|
| 45-16692 | 6/1970 | Japan | 260/326.5 FL |
| 45-28769 | 9/1970 | Japan | 260/326.5 FL |
| 48-561 | 1/1973 | Japan | 260/326.5 FL |

*Primary Examiner*—Alan L. Rotman
*Assistant Examiner*—Robert C. Whittenbaugh
*Attorney, Agent, or Firm*—Wenderoth, Lind & Ponack

[57] ABSTRACT

Compounds of formula:

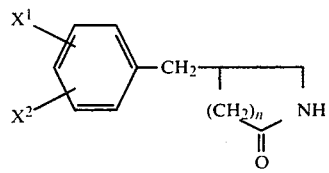

wherein $X^1$ is a halogen atom, $X^2$ is a halogen atom or hydrogen atom, n is 1 or 2 are novel compounds and useful as anti-anxiety agents.

12 Claims, No Drawings

LACTAM COMPOUNDS

This invention relates to novel lactam compounds which are of value as anti-anxiety agents.

More particularly, this invention relates to lactam compounds having the general formula:

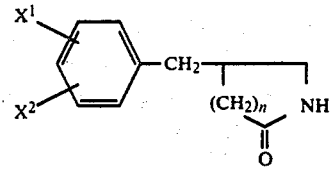

wherein $X^1$ is a halogen atom, $X^2$ is a halogen atom or hydrogen atom and n is 1 or 2.

Referring to the above general formula (I), the halogen atom represented by $X^1$ and $X^2$ may for example be fluorine, chlorine, bromine, etc. The compounds of the general formula (I) may have a substituent or substituents, which are the same or different, at any position of the phenyl ring.

The compounds according to this invention have an activity on the central nervous system, and has been found to exert strong anti-anxiety actions in anti-conflict tests in rats. The minimum lethal dosed (MLD) of these compounds are not less than 500 mg/kg in mice and the minimum effective doses (MED) in rats are not more than 2.5 mg/kg, thus indicating a very broad drug safety range. Moreover, compared with benzodiazepine preparations which are now commercially available as anxiety remedies, these compounds are only very mildly hypnotic and muscle-relaxant as side-effects. Therefore, the compounds of this invention are of value as anti-anxiety drugs. The compounds are of use in the treatment of such diseases as anxiety neurosis and various psychosomatic diseases such as autonomic instability, neurotic emesis, neurodermatitis, alopecia areata, angina pectoris nervosa, dyspnoeneurosis, etc.

The present compounds have anticonvulsant activity as well and, therefore, are of use in the management of epilepsy, traumatic epilepsy, etc. The compounds are administered to man and other mammalian animals, orally or by other routes, in such dosage forms as tablets, granules, capsules, parenteral injections, suppositories and so forth. While the proper dosage depends on the type of the disease, condition, etc., these compounds are normally used in the daily dose of about 0.001 to 50 mg/kg body weight, preferably about 0.1 to 50 mg/kg body weight in the case of animals and in the daily dose of 0.1 to 100 mg, preferably 0.5 to 20 mg, in the case of human adults.

The compounds according to this invention can be produced, for example through the following steps.

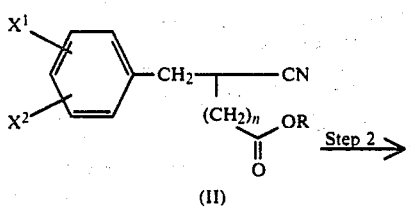

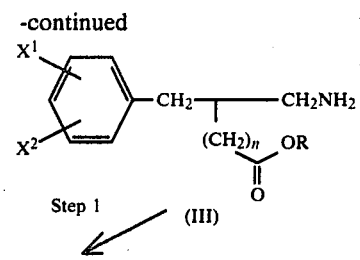

[wherein $X^1$, $X^2$, and n have respectively the same meaning as defined hereinbefore, and R is hydrogen or an alkyl group having 1 to 4 carbon atoms, e.g. methyl, ethyl, propyl, iso-propyl, n-butyl, iso-butyl, tert.-butyl, etc.]

The reaction involved in Step 1 comprises subjecting the compound (III) to cyclization reaction. This cyclization reaction takes place in neutral or alkaline conditions. When compound (III) is its acid addition salt, a base is added to a solution of the salt of compound (III) in a suitable solvent to make a reaction system neutral or alkaline conditions. As examples of said base there may be mentioned alkali metal hydroxides such as sodium hydroxide, potassium hydroxide, etc. alkaline earth metal hydroxides such as barium hydroxide, etc. and alkali metal alkoxides such as sodium methoxide, sodium ethoxide, potassium methoxide, potassium ethoxide, etc. The base is desirably employed in a proportion of about 1 to 1.2 equivalents based on the salt of compound (III). As examples of the solvent there may be mentioned water and alcohols (e.g. methanol, ethanol, propanol, etc.). While the reaction proceeds satisfactorily at room temperature, it may be conducted under cooling or heating if desired.

The lactam compound (I) thus obtained can be isolated and purified by known separation procedures such as e.g. concentration, distillation, pH adjustment, solvent extraction, crystallization, recrystallization, phasic transfer and chromatography.

The reaction involved in Step 2 is carried out by subjecting a compound (II) to reduction reaction.

The reduction procedure may normally be conducted catalytically.

The catalytic reduction procedure comprises passing hydrogen gas into a solvent solution of the substrate compound (II) and a catalyst which is normally employed for usual catalytic reduction purposes. As examples of such catalyst, there may be mentioned palladium-on-carbon, palladium-on-barium carbonate, Raney's nickel and platinum oxide.

The catalyst is employed in an amount ranging from 0.1 to 1.5 times the weight of compound (II), preferably 0.5 to 1.0 times the weight of compound (II). As examples of said solvent there may be mentioned alcohols, e.g. methanol, ethanol, propanol, butanol, etc.; alkyl esters of acetic acid, e.g. ethyl acetate, propyl acetate, butyl acetate, etc.; ethers, e.g. dioxane, tetrahydrofuran, etc.; and acetic acid.

While this reaction proceeds even at atmospheric pressure, it is desirably conducted at an elevated pressure not over 150 kg/cm². The reaction temperature may range from 0° to 100° C. and, preferably, 30° to 80° C. The reaction time is normally within the range of 2 to 5 hours, although it depends on the type of catalyst and the pressure used.

When the reduction is conducted under acidic condition, compound (III) is obtained as its acid addition salt.

As the acids employable for formation of the acid addition salts, there may be mentioned mineral acid such as hydrochloric acid, hydrobromic acid, sulfuric acid and phosphoric acid, although hydrochloric acid and hydrobromic acid are particularly desirable. The reduction procedure may normally be catalytic reduction.

The acid addition salts of compound (III) may be subjected as such to step 1 without isolating from the reaction mixture.

When the reduction is conducted under neutral or alkaline conditions, compound (III) thus formed is immediately cyclized to give the compound (I).

The compound (II) can be prepared, for example, by heating a compound of general formula:

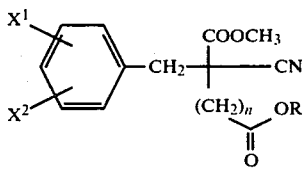
(IV)

[wherein $X^1$, $X^2$, R, and n are respectively as defined hereinbefore] in a solvent such as dimethylsulfoxide and in the presence of sodium chloride and a small amount of water at an elevated temperature such as about 180° C.

The compound (IV) can be prepared, for example by reacting a compound of general formula:

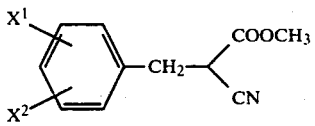
(V)

[wherein $X^1$ and $X^2$ have the same meaning as defined above] with a compound of general formula:

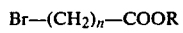
Br—$(CH_2)_n$—COOR (VI)

[wherein R and n have the same meaning as defined above] in a solvent such as benzene or toluene and in the presence of sodium ethoxide at a temperature ranging from room temperature to 100° C.

The following examples are given to illustrate this invention in further detail.

EXAMPLE 1

(a) To a mixture of 223 g of ethyl 2-cyano-p-chlorocinnanate and 1.2 l of ethanol was added 10.4 g of sodium borohydride in small installments with constant stirring and ice-cooling, followed by stirring at room temperature for 2 hours. After the reaction, the solvent was distilled off under reduced pressure and the residue was dissolved in ethyl acetate, washed with water, 2% hydrochloric acid and water in the order mentioned, dehydrated over sodium sulfate and concentrated under reduced pressure. The residue was purified by distillation to obtain ethyl 3-(4-chlorophenyl)-2-cyanopropionate.

Yield 186.5 g; b.p. 140°–145° C./0.4 Torr.

Elemental analysis, for $C_{12}H_{12}ClNO_2$; Calcd. C, 62.63; H, 5.09; N, 5.89; Found C, 62.68; H, 4.91; N, 5.78.

(b) To sodium ethoxide (prepared from 5.1 g sodium metal) was added 47.5 g of ethyl 3-(4-chlorobenzyl)-2-cyanopropionate as dissolved in 500 ml of toluene, the resultant mixture was heated and the byproduct ethanol was distilled off. The residue was heated with the addition of toluene and 50 ml of the solvent was distilled off at the boiling point of toluene. The solution was cooled to 50° C. and, under stirring, 33.5 g of ethyl bromoacetate was added and the mixture refluxed for 3 hours. The reaction mixture was added to ice-water, the organic layer was separated, the aqueous layer was extracted twice with ethyl acetate and the extracts were pooled with the organic layer. The organic layer was washed with water, 2% sodium hydroxide, water, 2% hydrochloric acid and water in the order mentioned, dehydrated and concentrated under reduced pressure.

The residue was purified by distillation to obtain ethyl 4-(4-chlorophenyl)-3-cyano-3-ethoxycarbonylbutyrate.

Yield 48.9 g; b.p. 180°–185° C./0.3 Torr.

Elemental analysis, for $C_{16}H_{18}ClNO_4$; Calcd. C, 59.35; H, 5.60; N, 4.33; Found C, 59.52; H, 5.56; N, 4.41.

(c) In 50 ml of dimethylsulfoxide was dissolved 48.9 g of ethyl 4-(4-chlorophenyl)-3-cyano-3-ethoxycarbonylbutyrate and, after the addition of 8.8 g of sodium chloride and 2.7 ml of water, the solution was refluxed at 180° C. for 2 hours.

The reaction mixture was added to ice-water and extracted with ether. The extract was washed with water, 2% aqueous sodium hydroxide, water, 2% hydrochloric acid and water in the order mentioned, dehydrated and concentrated. The residue was purified by distillation to obtain ethyl 4-(4-chlorophenyl)-3-cyanobutyrate.

Yield 27.1 g; b.p. 160°–163° C./0.2 Torr.

Elemental analysis, for $C_{13}H_{14}ClNO_2$; Calcd. C, 62.03; H, 5.61; N, 5.57; Found C, 61.96; H, 5.73; N, 5.36.

(d) In 100 ml of ethanol was dissolved 5 g of ethyl 4-(4-chlorophenyl)-3-cyanobutyrate and, with 10 ml of Raney's nickel as the catalyst, reduction was carried out in hydrogen gas streams for 2 hours. The catalyst was removed by decanting and the solvent was distilled off under reduced pressure. The residue was dissolved in ethyl acetate, washed with water, 2% aqueous sodium hydroxide, water, 2% hydrochloric acid and water in the order mentioned, dehydrated and concentrated under reduced pressure. The residue was crystallized from ether-n-hexane to obtain the contemplated product 4-(4-chlorobenzyl)-2-pyrrolidinone.

Yield 2.6 g; m.p. 95°–98° C.

Elemental analysis, for $C_{11}H_{12}ClNO$; Calcd. C, 63.01; H, 5.77; N, 6.68; Found C, 62.80; H, 5.73; N, 6.47.

EXAMPLE 2

(a) In the same manner as Example 1-(a), 200 g of ethyl 2-cyano-o-chlorocinnamate was reduced with 10.6 g of sodium borohydride in methanol to obtain methyl 3-(2-chlorophenyl)-2-cyanopropionate.

Yield 158.6 g; b.p. 130°–135° C./0.3 Torr.

Elemental analysis, for $C_{11}H_{10}ClNO_2$; Calcd. C, 59.07; H, 4.51; N, 6.26; Found C, 58.91; H, 4.80; N, 6.28.

(b) In the same manner as Example 1-(b), 100 g of methyl 3-(2-chlorophenyl)-2-cyanopropionate was reacted with methyl bromoacetate to obtain methyl 4-(2-chlorophenyl)-3-cyano-3-methoxycarbonylbutyrate.

Yield 103 g; b.p. 165°–170° C./0.3 Torr.

Elemental analysis, for $C_{14}H_{14}ClNO_2$; Calcd. C, 56.86; H, 4.77; N, 4.74; Found C, 56.92; H, 4.51; N, 4.63.

(c) In the same manner as Example 1-(c), 50 g of methyl 4-(2-chlorophenyl)-3-cyano-3-methoxycarbonylbutyrate was decarboxylated in dimethylsulfoxide to obtain methyl 4-(2-chlorophenyl)-3-cyanobutyrate.

Yield 38 g; b.p. 147°–149° C./0.3 Torr.

Elemental analysis, for $C_{12}H_{12}ClNO_2$; Calcd. C, 60.63; H, 5.09; N, 5.89;

Found C, 60.78; H, 5.30; N, 5.71.

(d) In the same manner as Example 1-(d), 10 g of methyl 4-(2-chlorophenyl)-3-cyanobutyrate was catalytically reduced with the aid of Raney's nickel to obtain 4-(2-chlorobenzyl)-2-pyrrolidinone.

Yield 4.6 g; m.p. 87°–89° C.

Elemental analysis, for $C_{11}H_{12}ClNO$; Calcd. C, 63.01; H, 5.77; N, 6.68; Found C, 63.03; H, 5.67; N, 6.56.

EXAMPLE 3

(a) In the same manner as Example 1-(a), 33.6 g of ethyl 2-cyano-m-chlorocinnamate was reduced with sodium borohydride in methanol to obtain methyl 3-(3-chlorophenyl)-2-cyanopropionate. Yield 26.9 g; b.p. 138°–140° C./0.3 Torr.

Elemental analysis, for $C_{11}H_{10}ClNO_2$; Calcd. C, 59.07; H, 4.51; N, 6.26; Found C, 59.31; H, 4.48; N, 6.05.

(b) In the same manner as Example 1-(b), 26.5 g of methyl 3-(3-chlorophenyl)-2-cyanopropionate was reacted with methyl bromoacetate to obtain methyl 4-(3-chlorophenyl)-3-cyano-3-methoxycarbonylbutyrate.

Yield 24.8 g; b.p. 168°–171° C./0.3 Torr.

Elemental analysis, for $C_{14}H_{14}ClNO_4$; Calcd. C, 56.86; H, 4.77; N, 4.74; Found C, 57.17; H, 4.71; N, 4.73.

(c) In the same manner as Example 1-(c), 24 g of methyl 4-(3-chlorophenyl)-3-cyano-3-methoxycarbonylbutyrate was decarboxylated to obtain methyl 4-(3-chlorophenyl)-3-cyanobutyrate.

Yield 14 g; b.p. 147°–149° C./0.3 Torr.

Elemental analysis, for $C_{12}H_{12}ClNO_2$; Calcd. C, 60.63; H, 5.09; N, 5.89; Found C, 60.88; H, 5.13; N, 5.73.

(d) In the same manner as Example 1-(d), 5 g of methyl 4-(3-chlorophenyl)-3-cyanobutyrate was reduced with Raney's nickel as the catalyst to obtain 4-(3-chlorobenzyl)-2-pyrrolidinone.

Yield 1.6 g; m.p. 117°–119° C.

Elemental analysis, for $C_{11}H_{12}ClNO$; Calcd. C, 63.01; H, 5.77; N, 6.68; Found C, 62.80; H, 5.67; N, 6.59.

EXAMPLE 4

(a) In the same manner as Example 1-(a), 68 g of ethyl 2-cyano-m.p-dichlorocinnamate was reduced with sodium borohydride in methanol to obtain methyl 2-cyano-(2,4-dichlorophenyl)propionate.

Yield 45 g; b.p. 145°–150° C./0.2 Torr.

Elemental analysis, for $C_{11}H_9Cl_2NO_2$; Calcd. C, 51.19; H, 3.51; N, 5.43; Found C, 51.26; H, 3.42; N, 5.33.

(b) In the same manner as Example 1-(b), 44.9 g of methyl 2-cyano-(2,4-dichlorophenyl)propionate was reacted with methyl bromoacetate to obtain methyl 3-cyano-4-(2,4-dichlorophenyl)-3-methoxycarbonylbutyrate.

Yield 45.6 g; b.p. 185°–190° C./0.3 Torr.

Elemental analysis, for $C_{14}H_{13}Cl_2NO_4$; Calcd. C, 50.93; H, 3.97; N, 4.24; Found C, 51.11; H, 3.92; N, 4.28.

(c) In the same manner as Example 1-(c), 34.6 g of methyl 3-cyano-4-(2,4-dichlorophenyl)-3-methoxycarbonylbutyrate was decarboxylated to obtain methyl 3-cyano-4-(2,4-dichlorophenyl)butyrate.

Yield 20.2 g; m.p. 86°–88° C.

Elemental analysis, for $C_{12}H_{11}Cl_2NO_2$; Calcd. C, 52.96; H, 4.08; N, 5.15;

Found C, 52.97; H, 3.96; N, 5.09.

(d) In the same manner as Example 1-(d), 5 g of methyl 3-cyano-4-(2,4-dichlorophenyl)butyrate was reduced with the aid of Raney's nickel to obtain the contemplated product 4-(2,4-dichlorobenzyl)-2-pyrrolidinone.

Yield 2.9 g; m.p. 85°–86° C.

Elemental analysis, for $C_{11}H_{11}Cl_2NO$; Calcd. C, 54.12; H, 4.54; N, 5.74; Found C, 54.16; H, 4.45; N, 5.85.

EXAMPLE 5

(a) In the same manner as Example 1-(b), 47.5 g of ethyl 3-(4-chlorophenyl)-2-cyanopropionate was reacted with ethyl 2-bromopropionate to obtain ethyl 5-(4-chlorophenyl)-4-cyano-4-ethoxycarbonylvalerate.

Yield 48.9 g; b.p. 180°–185° C./0.3 Torr.

Elemental analysis, for $C_{17}H_{20}ClNO_4$; Calcd. C, 60.44; H, 5.97; N, 4.15; Found C, 60.21; H, 5.98; N, 3.92.

(b) In the same manner as Example 1-(c), 32 g of ethyl 5-(4-chlorophenyl)-4-cyano-4-ethoxycarbonylvalerate was decarboxylated to obtain ethyl 5-(4-chlorophenyl)-4-cyanovalerate.

Yield 21 g; b.p. 165°–170° C./0.3 Torr.

Elemental analysis, for $C_{14}H_{16}ClNO_2$; Calcd. C, 63.27; H, 6.07; N, 5.27; Found C, 63.16; H, 5.91; N, 5.36.

(c) In the same manner as Example 1-(d), 5 g of ethyl 5-(4-chlorophenyl)-4-cyanovalerate was reduced with Raney's nickel as the catalyst to obtain 5-(4-chlorobenzyl)-2-piperidinone.

Yield 1.8 g; m.p. 118°–120° C.

Elemental analysis, for $C_{12}H_{12}ClNO$ ; Calcd. C, 64.43; H, 6.31; N, 6.26; Found C, 64.73; H, 6.26; N, 6.03.

EXAMPLE 6

(a) In the same manner as Example 1-(a), 200 g of ethyl 2-cyano-p-fluorocinnamate was reduced with 10.0 g of sodium borohydride in ethanol to obtain ethyl 3-(4-fluorophenyl)-2-cyanopropionate.

Yield 149.3 g; b.p. 137°–140° C./0.3 Torr.

Elemental analysis, for $C_{12}H_{12}FNO_2$; Calcd. C, 65.14; H, 5.47; N, 6.33; Found C, 65.30; H, 5.66; N, 6.31.

(b) In the same manner as Example 1-(b), 100 g of ethyl 3-(4-fluorophenyl)-2-cyanopropionate was reacted with ethyl bromoacetate to obtain ethyl 4-(4-fluorophenyl)-3-cyano-3-ethoxycarbonylbutyrate.

Yield 98 g; b.p. 165°–170° C./0.3 Torr.

Elemental analysis, for $C_{16}H_{18}FNO_4$; Calcd. C, 62.53; H, 5.90; N, 4.56; Found C, 62.49; H, 5.91; N, 4.50.

(c) In the same manner as Example 1-(c), 50 g of ethyl 4-(4-fluorophenyl)-3-cyano-3-ethoxycarbonylbutyrate was decarboxylated in dimethylsulfoxide to obtain ethyl 4-(4-chlorophenyl)-3-cyanobutyrate.

Yield 37 g. b.p. 145°–150° C./0.3 Torr

Elemental analysis, for $C_{13}H_{14}FNO_2$; Calcd. C, 66.37; H, 6.00; N, 5.96; Found C, 66.52; H, 6.09; N, 5.67.

(d) In the same manner as Example 1-(d), 10 g of ethyl 4-(4-fluorophenyl)-3-cyanobutyrate was catalytically reduced with the acid of Raney's nickel to obtain 4-(4-fluorobenzyl)-2-pyrrolidinone.

Yield 5.0 g. m.p. 88.5°–90° C.

Elemental analysis, for $C_{11}H_{12}FNO$; Calcd. C, 68.37; H, 6.26; N, 7.25; Found C, 68.50; H, 6.19; N, 7.03.

What is claimed is:

1. A compound of the formula:

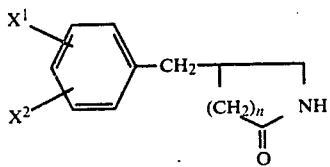

wherein $X^1$ is a halogen atom, $X^2$ is a halogen atom or hydrogen atom, and n is 1 or 2.

2. A compound as claimed in claim 1, wherein n is 1.

3. A compound as claimed in claim 1, wherein n is 2.

4. A compound as claimed in claim 1, wherein $X^2$ is hydrogen atom.

5. A compound as claimed in claim 1, wherein $X^2$ is a halogen atom.

6. A compound as claimed in claim 1, wherein $X^1$ and $X^2$ are chlorine.

7. A compound as claimed in claim 1, wherein the compound is 4-(4-chlorobenzyl)-2-pyrrolidinone.

8. A compound as claimed in claim 1, wherein the compound is 4-(2-chlorobenzyl)-2-pyrrolidinone.

9. A compound as claimed in claim 1, wherein the compound is 4-(3-chlorobenzyl)-2-pyrrolidinone.

10. A compound as claimed in claim 1, wherein the compound is 4-(2,4-dichlorobenzyl)-2-pyrrolidinone.

11. A compound as claimed in claim 1, wherein the compound is 5-(4-chlorobenzyl)-2-piperidinone.

12. A compound as claimed in claim 1, wherein the compound is 4-(4-fluorobenzyl)-2-pyrrolidinone.

* * * * *